United States Patent [19]

Favstritsky

[11] Patent Number: 4,886,915

[45] Date of Patent: Dec. 12, 1989

[54] WATER SOLUBLE ORGANIC AMMONIUM PER HALIDES

[75] Inventor: Nicolai A. Favstritsky, Lafayette, Ind.

[73] Assignee: Great Lakes Chemical Corporation, West Lafayette, Ind.

[21] Appl. No.: 211,362

[22] Filed: Jun. 24, 1988

[51] Int. Cl.$^4$ .................. C07C 87/22; C07C 91/04
[52] U.S. Cl. .................................. 564/503; 564/1; 564/462; 564/463; 564/504; 564/505; 564/508; 564/510; 564/511
[58] Field of Search .................. 564/1, 462, 463, 503, 564/504, 505, 508, 510, 511

[56] References Cited

U.S. PATENT DOCUMENTS 3,152,073  10/1964  Morton ........................... 210/62

FOREIGN PATENT DOCUMENTS 8802351  4/1987  PCT Int'l Appl.

OTHER PUBLICATIONS

John, "Bromine and Its Compounds", Part II, Chapter I, pp. 113–114.

Chattaway, et al., Journal of Chemical Society, vol. 123, pp. 654–662 (1923).

Mercier et al., Proceedings of the National Academy of Science, U.S., vol. 42, pp. 65–67 (1956).

Popov, et al., Inorganic Synthesis, vol. 5, pp. 176–178 (1957).

Romers, et al., Proceedings of the Koninklijke Nederlandse Akademie, vol. B61, pp. 345–346 (1958).

Primary Examiner—Richard L. Raymond
Attorney, Agent, or Firm—Kirkland & Ellis

[57] ABSTRACT

Water soluble biocidal water treatment perhalides of the formula:

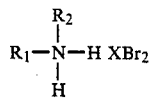

where $R_1$ and $R_2$ are independently hydrogen, hydroxyethyl, alkyl, cyclic alkyl, (alpha, omega)-alkyl, alkyl ether, polyether, heterocyclic ring-substituted alkyl, and halogenated alkyl; X is chlorine, bromine or iodine; and only one of $R_1$ and $R_2$ may be hydrogen.

6 Claims, No Drawings

WATER SOLUBLE ORGANIC AMMONIUM PER HALIDES

BACKGROUND OF THE INVENTION

1. Field of the Invention

The present invention relates to novel, organic ammonium perhalides which are stable, water soluble and possess high concentrations of easily available oxidizing bromine. More particularly, this invention relates to stable, water soluble organic ammonium perhalides which have utility as water sterilization agents.

2. Description of the Art

Generally, materials which deliver oxidizable bromine have rather low water solubility, as exemplified by elemental bromine, bromine chloride and N-halogenated organics. On the other hand, materials which are water soluble, such as alkali metal bromides, require another powerful oxidizing reagent to effect the release of oxidizable bromine.

The prior art has disclosed compounds of the following Structure I:

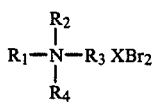

where $R_1$–$R_4$ are various organic substituents, no more than one of $R_{1-4}$ being hydrogen, and X is chlorine, bromine or iodine.

Structure I, where $R_1$–$R_4$ are all hydrogen, is ammonium perhalide: $NH_4XBr_2$. D. H. O. John [in "Bromine and its Compounds," edited Z. E. Jolles, Part II, Chapter 1, page 114, Academic Press, New York, 1966]states that $NH_4Br_3$ can be obtained by the electrolysis of a concentrated solution of ammonium bromide. A more direct method of obtaining $NH_4Br_3$, mentioned by John, is to dissolve bromine in ammonium bromide solution. The prior art does not show any use or application for this compound.

Structure I where $R_4$ is hydrogen, $R_1R_2R_3NHXBr_2$, also known as trisubstituted amine hydrotrihalides, is disclosed by Mercier, et al., [Proceedings of the National Academy of Science, U.S., Volume 42 pages 65 to 67 (1956)], who reported that quaternary and ternary alkylammonium chlorides and bromides dissolve readily in bromine with formation of low melting complexes. The authors gave melting points for the following perhalides:

$Bu_4NBr.Br_2$ (m 76°), $Bu_4NBr.3Br_2$ (m 37°), $Me_3NHCl.Br_2$ (m 37°), $Me_3NHCl.2Br_2$ (m 11.5°), $Me_3NHCl.4Br_2$ (m 11.5°), $Me_3NHBr.Br_2$ (m 34°), $Me_3NHBr.2Br_2$ (m 6°), $Me_3NHBr.3Br_2$ (m 1.5°) $AM_3NHCl.Br_2$ (m 33°)

Also, C. Romers and E. W. M. Keulemans [Proceedings of the Koninklijke Nederlandse Akademie, Volume B61, pages 345–346, 1958]cited $(CH_3)_3NHBr_3$ as one of the compounds formed when bromine is added to the $CCl_4$ solution of trimethylamine. The mechanism of its formation is not given, however.

Finally, Structure I, where none of the substituents are hydrogen, $R_1R_2R_3R_4NBrX$, yields tetrasubstituted ammonium perhalides. Tetraalkylammonium perhalides are well known to the prior art. Two references detail the preparation of this class of compounds: (1) Frederick D. Chattaway and George Hoyle, *Journal of Chemical Society*, Volume 123, pages 655 to 662, 1923; and (2) Alexander I. Popov and Robert E. Buckles, *Inorganic Synthesis*, Volume V, pages 176 to 178, McGraw-Hill Book Company, Inc. New York, 1957.

Morton, U.S. Pat. No. 3,152,073 describes the use of tetramethylammonium chlorodibromide for sterilizing water. Morton goes on to disclose a wide variety of tetraalkylammonium polyhalides which contain alkyl groups of six or fewer carbons, suggesting that they may be used as single reagents, directly added to water, to achieve sterilization. It has now been found that, in fact, many of Morton's compounds are not sufficiently soluble in water for use by the method disclosed.

Gannon, et al., U.S. patent application Ser. No. 048,902, filed Apr. 20, 1987, now abandoned, discloses water sterilization compositions and methods using tetrasubstituted ammonium perhalides as well as trisubstituted amine hydrotribromides. The utility of these compositons and methods has been inhibited by the poor water solubility of the compounds.

Accordingly, a primary objective of this invention is to overcome the disadvantages of the prior art materials.

A further object is to provide a composition and method of synthesis for novel organosubstituted water-soluble perbromides.

Another is to provide compositions of the character described having utility as biocidal additives in aqueous systems.

SUMMARY OF THE INVENTION

The foregoing and other objects, advantages and features of the present invention may be achieved with water soluble mono- and di-substituted ammonium perhalide compounds of the formula:

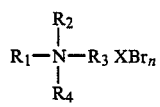

where $R_1$ and $R_2$ are independently hydrogen or organic substituents, with only one of $R_1$ and $R_2$ being hydrogen; and $R_3$ and $R_4$ are hydrogen; and n is 2 to 6. More particularly, the compounds of the present invention include compounds of the following general formulae: $R_1R_2NH_2XBr_n$ and $R_1NH_3XBr_n$, where $R_1$ and $R_2$ are independently hydrogen, hydroxyethyl, alkyl, cyclic alkyl, (alpha, omega)-alkyl, alkyl ether, polyether, heterocyclic ring-substituted alkyl, and halogenated alkyl; X is chlorine, bromine or iodine; n is 2 to 6; and only one of $R_1$ and $R_2$ can be hydrogen. These mono- and disubstituted ammonium perhalides possess high concentrations of oxidizable bromine, are stable, have good water solubility and can be easily prepared.

DESCRIPTION OF THE PREFERRED EMBODIMENTS

The water soluble mono- and di-substituted ammonium perhalides of this invention are compounds of of the following structure:

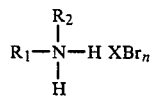

where $R_1$ and $R_2$ are independently hydrogen, hydroxyethyl, alkyl, cyclic alkyl, (alpha, omega)-alkyl, alkyl ether, polyether, heterocyclic ring-substituted alkyl, and halogenated alkyl; X is chlorine, bromine or iodine; n is 2 to 6; and only one of $R_1$ and $R_2$ may be hydrogen. These perhalide compounds may be prepared by reacting the corresponding mono- or di-substituted ammonium hydrohalide salt with bromine.

The solubility and bromine content of the compounds depend on the bulk and nature of the substituents. The most preferred substituents are $R_1$ = hydroxyethyl, $C_1$ to $C_8$ alkyl groups, and $R_2$ = hydrogen, hydroxyethyl, or $C_1$ to $C_8$ alkyl groups.

In general, the compounds of this invention include mono- and di-substituted perhalides where X may be chlorine or iodine. It is preferred, however, to employ compounds where X is bromine, that is perbromides of the formula $R_1R_2NH_2$—$Br_3$.

Specific stable, water soluble perhalides useful with the method of the present invention include ethanolammonium perbromide, propylammonium perbromide, diethanolammonium perbromide, butylammonium perbromide, methylethanolammonium per bromide, ethylethanolammonium perbromide, hexylammonium perbromide octylammonium perbromide, dipropylammonium perbromide, dibutylammonium perbromide, diethylammonium perbromide, 1,6-hexanediammonium perbromide, as well as the corresponding chloro and iodo-dibromides.

If desired, the shelf life of aqueous solutions of the compounds of this invention may be stabilized by increasing the amount of ammonium hydrohalide in relation to bromine. More particularly, up to four moles of mono- or di-substituted ammonium hydrohalide salt may be admixed with one mole of bromine. Perhalides with lower apparent vapor pressure and lower oxidizable bromine content are produced when two moles of salt in aqueous solution are added to one mole of elemental bromine. Mono- and di-substitued ammonium hydrohalide salts which may be used include those of the formula:

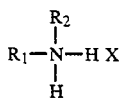

where $R_1$ and $R_2$ are independently hydrogen, hydroxyethyl, alkyl, cyclic alkyl, (alpha, omega)-alkyl, alkyl ether, polyether, heterocyclic ring-substituted alkyl, and halogenated alkyl; X is chlorine, bromine, or iodine; and only one of $R_1$ and $R_2$ may be hydrogen.

Shelf life stability may also be increased by replacing part of the substituted ammonium hydrohalide salt with other stability enhancing salts such as alkali metal and ammonium bromides, especially ammonium bromide and sodium bromide, preferably in a molar ratio of about 1:1.

Preferably, the substituted ammonium hydrohalide salt and other stability enhancing salt, if any, are provided in a ratio lying in the range of about 1 to 4 moles of salt to 1 mole of bromine.

Further, it may be convenient to blend the compounds of this invention with water to produce a liquid mixture which can be easily handled by pumping and metering devices

PREPARATION OF THE COMPOUNDS OF THIS INVENTION

The compounds of this invention can be easily prepared by first reacting the corresponding amines with hydrogen halide (Equation 1), followed by the addition of bromine (Equation 2):

(1) $R_1R_2NH + HX \rightarrow R_1R_2NH_2X$ (2) $R_1R_2NH_2X + Br_2 \rightarrow R_1R_2NH_2XBr_2$ Most conveniently, an aqueous solution of lower alkyl- or dialkyl-ammonium perbromides can be prepared by reacting the readily available and inexpensive aqueous 48% hydrobromic acid with neat amine. The resulting aqueous amine hydrobromic salt is then readily converted to the perbromide by the addition of bromine. A simple one-pot procedure produces aqueous solutions of perbromides with exceedingly high bromine content.

Another method of preparing the same compound consists of first dissolving the bromine in hydrobromic acid, followed by the addition of the neat amine:

(3) $HBr + Br_2 \rightarrow HBr_3$ (4) $HBr_3 + R_1R_2NH \rightarrow R_1R_2NH_2XBr_2$ Still another method for the preparation of these compounds, especially if higher bromine content in the solution is desired, consists of reacting a more concentrated hydrobromic acid with amine, followed by bromine addition. Alternatively, the corresponding aqueous solution of the amine hydrobromide can be concentrated by evaporating water, followed by the addition of appropriate amount of bromine.

Finally, anhydrous perbromides can also be easily prepared by gently heating the dry amine hydrobromide salt with bromine.

Analogous procedures may be employed to produce the chlorine and iodine containing perhalides of this invention by employing the corresponding hydrogen halide in the foregoing reactions.

The perhalides of this invention include those containing additional bromine. The bromine content of these perhalides may be increased by adding more than one mole of bromine to the substituted-ammonium hydrobromide, yielding a higher perbrominated salt, as illustrated by Equation (5).

(5) $R_1R_2NH_2Br + 2Br_2 \rightarrow R_1R_2NH_2Br_5$

Although four or more moles of bromine can be added to the aqueous amine hydrobromide, the solution, upon contact with excess water, releases elemental bromine. However, it is possible to prepare solutions of perbromides in which the bromine content approached $R_1R_2NH_2Br_5$ and which did not release bromine upon contact with excess water.

SHELF LIFE STABILITY OF AQUEOUS PERBROMIDES

Aqueous solutions of perhalides have surprisingly good shelf life stability. Generally, in aqueous solution, monoalkylammonium perbromides are more stable than dialkylammonium perbromides. Furthermore, the more dilute the perbromide solution, the lower its stability unless stabilized with additional stabilizer additives.

In aqueous solution, the perhalides of this invention, though high in bromine content, show surprisingly low vapor pressure of bromine. Liquid elemental bromine has a vapor pressure of approximately 220 mm Hg at 26° C. and bromine water (containing approximately 3.5% by weight of bromine) shows a vapor pressure of 210 mm Hg at 26° C. These values can be compared to roughly 40-60 mm Hg measured for various perbromides containing roughly 40% oxidizable bromine. Again, for the sake of comparison, aqueous $NaBr_3$ containing roughly 40% $Br_2$ has a vapor pressure of 140 mm Hg. Of course, the vapor pressure of the aqueous perbromides of the present invention can be further reduced by the addition of ammonium or alkali metal bromide salts.

After the addition of the ethanolamine is completed, the reaction mixture (61.8% ethanolamine hydrobromide) is allowed to cool to room temperature. Then, bromine (1840 g./11.5 moles) is carefully added via an addition funnel, and the temperature is maintained below 5020 C. The yield of the dark red aqueous ethanolammonium perbromide is 4483 g.

The perbromide was then titrated for oxidizable bromine via the method described in "Standard Methods for the Examination of Water and Waste Water," 15th edition: Method 408A. Data for Compound #1 are given in Table 1.

Other water soluble organic ammonium perbromides identified as Compounds #2-9 in Table 1 were prepared via the procedure used for Compound #1, but on a reduced scale. Data for these compounds are also reported in Table 1.

TABLE 1

| Compound # | Name | Structure | Calc. Ox. $Br_2$* % by Weight | Tit. Ox. $Br_2$ % by Weight | Theo. Ox. $Br_2$** % by Weight |
|---|---|---|---|---|---|
| COMPLETELY SOLUBLE PERBROMIDES PREPARED FROM AQUEOUS SOLUTION | | | | | |
| 1 | Ethanolammonium Perbromide | $HOCH_2CH_2NH_3Br_3$ | 41.0 | 40.8 | 52.9 |
| 2 | Butylammonium Perbromide | $CH_3(CH_2)_3NH_3Br_3$ | 39.8 | 38.1 | 50.9 |
| 3 | Propylammonium Perbromide | $CH_3(CH_2)_2NH_3Br_3$ | 41.2 | 39.3 | 53.4 |
| 4 | Diethanolammonium Perbromide | $(HOCH_2CH_2)_2NH_2Br_3$ | 36.9 | 36.5 | 46.2 |
| 5 | Methylethanolammonium Perbromide | $(CH_3)(HOCH_2CH_2)NH_2Br_3$ | 39.5 | 39.3 | 50.6 |
| 6 | Ethylethanolammonium Perbromide | $(CH_3CH_2)(HOCH_2CH_2)NH_2Br_3$ | 38.1 | 37.7 | 48.4 |
| 7 | Dimethylethanolammonium Perbromide | $(CH_3)_2(HOCH_2CH_2)NHBr_3$ | 38.1 | 37.2 | 48.4 |
| 8 | Hexylammonium Perbromide | $CH_3(CH_2)_5NH_3Br_3$ | 37.2 | 36.1 | 46.7 |
| 9 | Octylammonium Perbromide | $CH_3(CH_2)_7NH_3Br_3$ | 34.9 | 34.7 | 43.2 |

*Oxidizable bromine calculated on an aqueous mass balance.
**Theoretical oxidizable bromine content of the neat compound The following examples will detail the preparation, properties and stability of the preferred perbromides in accordance with the present invention.

PREPARATION OF PERBROMIDES

Example 1

Compound #1: Ethanolammonium Perbromide

In a 5.0.1., four-necked round-bottom flask, immersed in an ice bath and equipped with a mechanical stirrer, reflux condenser, addition funnel, and thermometer, HBr (48%) (1940 g./11.5 moles) is placed. Ethanolamine (703 g./11.5 moles) is slowly added in at a rate such that the temperature does not exceed 50° C. to ensure minimal loss of HBr.

A series of additional perbromides identified as Compounds #10-14 were prepared using the procedure described above. However, after the addition of the bromine was completed, two liquid phases were produced. The top phase was an aqueous layer and contained a minimal amount of bromine. The bottom phase, a viscous liquid, represented the perbromide, which in most instances contained oxidizable bromine very close to the theoretical oxidizable bromine content of the neat compound. Data for Compounds 10-14 are given in Table 2.

TABLE 2

| Compound # | Name | Structure | Tit. Ox. Br % by Weight$^2$ | Theo. Ox. Br** % by Weight$^2$ | Solubility (g./100 g $H_2O$) |
|---|---|---|---|---|---|
| PARTIALLY SOLUBLE PERBROMIDES PREPARED FROM AQUEOUS SOLUTION | | | | | |
| 10 | Dipropylammonium Perbromide | $(CH_3(CH_2)_2)_2NH_2Br_3$ | 45.1 | 46.7 | 10 |
| 11 | Dibutylammonium Perbromide | $(CH_3(CH_2)_3)_2NH_2Br_3$ | 40.9 | 43.3 | 1.0 |
| 12 | Tributylammonium Perbromide | $(CH_3(CH_2)_3)_3NHBr_3$ | 36.0 | 37.5 | 0.01 |
| 13 | Triethylammonium Perbromide | $(CH_3CH_2)_3NHBr_3$ | 45.6 | 46.7 | 0.1 |
| 14 | Diethylethanolammonium | $(CH_3CH_2)_2(HOCH_2CH_2)NHBr_3$ | 42.3 | 44.7 | 0.1 |

**Theoretical oxidizable bromine content of the neat compound.

Compounds #15 and #16 were prepared using the foregoing procedure. The perbromides produced were crystalline solids which precipitated as the bromine addition proceeded. Data for Compounds 15 and 16 are shown in Table 3.

TABLE 3

| Compound # | Name | Structure | Tit. Ox. Br % by Weight[2] | Theo. Ox. Br** % by Weight[2] | Solubility (g./100 g H$_2$O) |
|---|---|---|---|---|---|
| 15 | Diethylammonium Perbromide | (CH$_3$CH$_2$)$_2$NH$_2$Br$_3$ | 47.9 | 50.9 | 15 |
| 16 | 1,6-Hexanediammonium | Br$_3$H$_3$N(CH$_2$)$_6$NH$_3$Br$_3$ | 51.8 | 53.5 | 50 |

**Theoretical oxidizable bromine content of the neat compound.

Compounds #7, #12, #13, #14, which are all trisubstituted amine hydroperbromides, were prepared for comparison purposes. All except Compound #7 are only sparingly soluble in water and thus are unsuitable for use where high water solubility is required. The water solubility of the perbromides which separated from the solution are shown in Tables 2 and 3. Again, with the exception of Compound #7, they are all significantly more soluble than the tri-substituted ammonium hydortribromides.

Example 2

Concentrated Organic Ammonium Perbromides

By concentrating the salt solution used, aqueous perbromides may be obtained with higher oxidizable bromine concentrations; These concentrated salt solutions may be prepared in two different ways: (1) the aqueous salt solution may be evaporated to the desired concentration; or (2) a more concentrated HBr may be used. The procedure for preparing a perbromide, using HBr (62%), is described below and the compound is listed as Compound #17 in Table 4.

Compound #17: Concentrated Aqueous Ethanolammonium Perbromide

Using the setup described in the preparation of Compound #1, HBr (62%) (500 g./3.8 moles) was placed in a round-bottom flask. Ethanolamine (234 g./3.8 moles) was slowly dripped into the flask. After the neutralization was complete, yielding a 74.1% salt solution, bromine (612 g./3.8 moles) was carefully dripped into the reaction flask.

Compound #18: Solid Anhydrous Ethanolammonium Perbromide

Ethanolammonium bromide (10 g./0.07-moles), prepared by the neutralization of HBr (48%) by ethanolamine and evaporated to dryness, was placed in a beaker. Bromine 11.2 g./0.07 moles) was added, and the beaker was covered with parafilm. The beaker was carefully heated to 35° C., at which point the contents of the beaker became a homogenous liquid. The beaker was allowed to sit overnight at room temperature (24° C.). By morning, the perbromide had crystallized.

Two other solid perbromides, solid propylammonium perbromide (Compound #19) and solid diethanolammonium perbromide (Compound #20), were very soluble in water and were prepared in the same manner (see Table 4).

Example 3

Perbromides with lower apparent vapor pressure and lower oxidizable bromine content are produced when two moles of the hydrobromide are salt are added to one mole of elemental bromine. If the second mole of salt is the same corresponding amine hydrobromide, then the perbromides are exemplified by Compounds #21-23. The procedure for preparing a 2:1 (salt:bromine) aqueous ethnolammonium perbromide (Compound #21) is described below. However, if the second salt is different, as exemplified by Compounds #24 and #25, then the desired second saltr can be added either as a solid or an aqueous solution, followed by the additon of bromine. The procedure for preparing Compound #24 is shown below. Data for Compounds #21-25 are given in Table 5.

TABLE 4

CONCENTRATED AND ANHYDROUS ORGANIC AMMONIUM PERBROMIDES

| Compound # | Name | Concentration of Hydrobromide % | Tit. Ox. Br % by Weight[2] | Calc. Ox. Br % by Weight[2] | M.P. (°C.) |
|---|---|---|---|---|---|
| 17 | Ethanolammonium Perbromide | 74.1 | 47.3 | 45.5 | Liquid |
| 18 | Ethanolammonium Perbromide | 100 | 51.8 | 52.9 | 47-53 |
| 19 | Propylammonium Perbromide | 100 | 53.2 | 53.4 | 25-29 |
| 20 | Diethanolammonium Perbromide | 100 | 45.3 | 46.2 | 35-45 |

Anhydrous Organic Perbromide.

TABLE 5

STABILIZED AQUEOUS ORGANIC AMMONIUM PERBOMIDES

| Compound # | Name | Stab. Salt Used | Tit. Ox. Br % by Weight[2] | Calc. Ox. Br % by Weight[2] |
|---|---|---|---|---|
| 21 | Ethanolammonium Perbromide | HOCH$_2$CH$_2$NH$_3$Br | 25.4 | 25.8 |
| 22 | Propylammonium Perbromide | CH$_3$(CH$_2$)$_2$NH$_3$Br | 26.9 | 28.6 |
| 23 | Diethanolammonium Perbromide | (HOCH$_2$CH$_2$)$_2$NH$_2$Br | 20.5 | 22.6 |
| 24 | Ethanolammonium Perbromide | NaBr | 24.4 | 24.8 |
| 25 | Ethanolammonium Perbromide | NH$_4$Br | 23.6 | 24.8 |

By using a completely anhydrous amine hydrobromide salt, it was possible to produce solid organic ammonium perbromides. Compound #18, shown in Table 4, is described below.

Compound #21: Aqueous 2:1 (Salt:Bromine) Ethanolammonium Perbromide

The ethanolamine hydrobromide salt is prepared via the neutralization of HBr (48%) with ethanolamine as described by Compound #1. Ethanoloamine hydrobromide (459.2 g./2.0 moles) is placed in a 500 ml round-bottom flask, equipped with a mechanical stirrer, thermometer, and addition funnel. Bromine (159.8 g/1 mole) is slowly added. A dark red liquid (612 g./98.9% yield based on mass balance) with very low visible vapor pressure is obtained.

Compound #24: Aqueous Ethanolammonium Perbromide Stabilized with NaBr

NaBr (26 g./0.25 moles) is dissolved in water (38 g.). The resulting solution is added to the ethanolammonium perbromide solution (100 g., containing 0.25 moles ethanolammonium hydrobromide and 0.25 moles of bromine). The perbromide produced has a very low vapor pressure.

Example 4

Higher Perbromides

Further addition of bromine to the aqueous organic ammonium perbromides is possible. These perbromides have a higher available oxidation bromine content and are still soluble in water. Data for these perbromides are listed in Table 6. The calculated n of $HOCH_2CH_2NH_3BrBr_n$ molecule is also shown. Compound #29, which had an added bromine concentration of approximately 51%, is the only perbromide that formed pools when a one-ml sample was placed in 200 ml of water.

TABLE 6

HIGHER AQUEOUS ETHANOLAMMONIUM PERBROMIDE

| Compound # | Grams $Br_2$ Added to 100 g Cpd #1 | Tit. Ox. $Br_2$ % by Weight | Calc. Ox. $Br_2$ % by Weight | $H_2O$ n1/ | Solubility |
|---|---|---|---|---|---|
| 26 | 24.6 | 52.6 | 52.5 | 3.2 | Completely |
| 27 | 46.9 | 57.7 | 59.7 | 4.3 | Completely |
| 28 | 69.0 | 63.9 | 65.0 | 5.5 | Completely |
| 29 | 106.0 | 72.6 | 71.3 | 7.3 | Formed pools |

1/n calculated for formula $HOCH_2CH_2NH_3BrBr_n$

Perbromide Shelf Life Stability Studies

In order to determine the shelf life stability of the perbromide solutions, a series of studies were conducted to determine the percent bromine lost over time. The following tables shown below list the perbromides studied and the percent oxidizable bromine lost over time. The perbromides studied were kept in closed bottles in ambient conditions (Table 7) and at 50° C. (Table 8).

TABLE 7

PERBROMIDE CLOSED-BOTTLE STABILITY AT AMBIENT TEMPERATURE

| Compound # | Name of Perbromide | Initial Ox. $Br_2$ % by Weight | Final Ox. $Br_2$ % by Weight | Change in % $Br_2$ | Relative Change in % $Br_2$ | Time Elapsed (months) |
|---|---|---|---|---|---|---|
| 1 | Ethanolammonium | 40.1 | 38.5 | 1.6 | 4.0 | 24 |
| 3 | Prophylammonium | 41.3 | 41.0 | 0.3 | 0.7 | 17 |
| 4 | Diethylammonium | 37.0 | 35.0 | 2.0 | 5.4 | 24 |
| 11 | Dibutylammonium | 43.2 | 41.1 | 2.1 | 4.9 | 16 |
| 21 | Stabilized Ethanolammonium | 25.4 | 24.9 | 0.5 | 2.0 | 24 |
| 22 | Stabilized Propylammonium | 25.6 | 25.0 | 0.6 | 2.3 | 24 |
| 23 | Stabilized Diethanolammonium | 22.1 | 19.7 | 2.4 | 10.9 | 22 |
| 30 | Diluted Compound #1 | 20.0 | 18.0 | 1.0 | 5.0 | 24 |
| 31 | Diluted Compound #3 | 20.0 | 18.2 | 1.8 | 9.0 | 24 |
| 32 | Diluted Compound #4 | 20.0 | 16.6 | 3.4 | 17.0 | 24 |

TABLE 8

PERBROMIDES CLOSED-BOTTLE STABILITY AT 50° C.

| Compound # | Name of Perbromide | Initial Ox. $Br_2$ % by Weight | Final Ox. $Br_2$ % by Weight | Change in % $Br_2$ | Relative Change in % $Br_2$ | Time Elapsed (months) |
|---|---|---|---|---|---|---|
| 1 | Ethanolammonium | 40.8 | 39.0 | 1.8 | 4.4 | 40 |
| 3 | Prophylammonium | 41.0 | 39.0 | 2.0 | 4.9 | 40 |
| 4 | Diethylammonium | 37.0 | 30.0 | 7.0 | 18.9 | 40 |
| 21 | Stabilized Ethanolammonium | 25.8 | 25.0 | 0.8 | 3.1 | 40 |
| 22 | Stabilized Propylammonium | 25.6 | 24.9 | 0.7 | 2.7 | 40 |
| 23 | Stabilized Diethanolammounium | 22.5 | 16.6 | 5.9 | 26.2 | 40 |
| 30 | Diluted Compound #1 | 20.0 | 17.2 | 2.8 | 14.0 | 40 |
| 31 | Diluted Compound #2 | 20.0 | 17.0 | 3.0 | 15.0 | 40 |
| 32 | Diluted Compound #3 | 20.0 | 10.6 | 9.4 | 47.0 | 40 |

Vapor Pressure of Perbromides

The vapor pressures of the aqueous organic ammonium perbromides were measured using an isoteniscope as described by Farrington, et al. [Farrington, D.; Alberti, R.; William, S.; Corwell, C.; Bender, P; and Harriman, S. *Experimental Physical Chemistry*, Experiment 17, pp. 164–165, 7th Edition, McGraw Hill Publishing Co., New York, 1976]. Data are reported in Table 9.

TABLE 9

VAPOR PRESSURE MEASUREMENTS OF ORGANIC AMMONIUM PERBROMIDES

| Compound # | Name of Perbromide | Ox. $Br_2$ % by Weight | Vp (mmHg @ 26° C.) |
|---|---|---|---|
| 1 | Ethanolammonium | 40.8 | 52 |
| 3 | Propylammonium | 39.3 | 36 |
| 4 | Diethylammonium | 36.5 | 49 |
| 5 | Methylethanolammonium | 39.3 | 28 |
| 7 | Dimethylethanolammonium | 37.2 | 30 |
| 11 | Dibutylammonium | 43.3 | 38 |
| 12 | Tributylammonium | 37.5 | 28 |

TABLE 9-continued

| Compound # | VAPOR PRESSURE MEASUREMENTS OF ORGANIC AMMONIUM PERBROMIDES | | |
|---|---|---|---|
| | Ox. Br$_2$ Name of Perbromide | % by Weight | Vp (mmHg @ 26° C.) |
| 17 | Conc. Ethanolammonium (62% HBr) | 47.3 | 57 |
| 21 | Stabilized Ethanolammonium | 25.4 | 36 |
| 27 | Bromine-loaded Ethanol-ammonium | 57.7 | 116 |
| 33 | Sodium (NaBr$_3$) | 37.9 | 145 |
| 34 | Bromine in H$_2$O | 3.5 | 210 |
| 35 | Pure Bromine | 100 | 223 |

The water soluble perhalides of this invention can be easily and economically prepared. They are surprisingly stable and have a high concentration of oxidizable bromine. This class of compounds is useful in all water treatment and other applications where stability and high bromine are desirable.

I claim:

1. Water soluble ammonium perhalides of the formula:

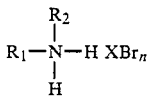

where $R_1$ and $R_2$ are independently hydrogen, hydroxyethyl, alkyl, cycloalkyl, alkyl ether, polyoxyalkylene, and halogenated alkyl; X is chlorine, bromine or iodine; n is 2 to 6; and only one of $R_1$ and $R_2$ may be hydrogen.

2. Water soluble perhalides, as claimed in claim 1, wherein X is bromine.

3. Water soluble perhalides, as claimed in claim 2, wherein $R_1$ is a member selected from the group consisting of hydroxyethyl and $C_{1-8}$ alkyl and $R_2$ is a member selected from the group consisting of hydrogen, hydroxyethyl and $C_{1-8}$ alkyl.

4. Ethanolammonium perbromide, $HOCH_2CH_2NH_313$ $Br_3$.

5. Propylammonium perbromide, $CH_3CH_2CH_2NH_3-Br_3$.

6. Diethanolammonium perbromide, $(HOCH_2CH_2)_2NH_2-Br_3$.

* * * * *

UNITED STATES PATENT AND TRADEMARK OFFICE
CERTIFICATE OF CORRECTION

PATENT NO. : 4,886,915
DATED : December 12, 1989
INVENTOR(S) : Nicolai A. Favstritsky It is certified that error appears in the above-identified patent and that said Letters Patent is hereby corrected as shown below:

Column 6, line 6   "5020 C." should be "50° C."

IN THE CLAIMS

Claim 4, line 21   "$HOCH_2CH_2NH_3 13\ Br_3$." should be "$HOCH_2CH_2NH_3\text{-}Br_3$."

Signed and Sealed this

Ninth Day of October, 1990

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO.   :   4,886,915

DATED        :   December 12, 1989

INVENTOR(S)  :   Nicolai A. Favstritsky

It is certified that error appears in the above-identified patent and that said Letters Patent is hereby corrected as shown below:

Column 6, line 6    "5020 C."    should be --50° C.--

IN THE CLAIMS

Claim 4, line 19    "HOCH$_2$CH$_2$NH$_3$13 Br$_3$."    should be --HOCH$_2$CH$_2$NH$_3$-Br$_3$.--

This certificate supersedes Certificate of Correction issued October 9, 1990.

Signed and Sealed this

Tenth Day of December, 1991

Attest:

HARRY F. MANBECK, JR.

*Attesting Officer*      *Commissioner of Patents and Trademarks*